United States Patent [19]
Incorvia et al.

[11] Patent Number: 5,962,333
[45] Date of Patent: Oct. 5, 1999

[54] MEDICAL DIAGNOSTIC TEST STRIP WITH DESICCANT

[75] Inventors: Samuel A. Incorvia, North Tonawanda; George E. McKedy, Amherst, both of N.Y.

[73] Assignee: Multisorb Technologies, Inc., Buffalo, N.Y.

[21] Appl. No.: 08/787,986

[22] Filed: Jan. 23, 1997

Related U.S. Application Data

[60] Provisional application No. 60/010,548, Jan. 25, 1996, and provisional application No. 60/016,996, Apr. 30, 1996.

[51] Int. Cl.$^6$ .................................................. G01N 33/48
[52] U.S. Cl. .............................. 436/169; 422/58; 422/57; 422/56
[58] Field of Search ................................ 422/56, 58, 61, 422/57; 436/164, 169, 170

[56] References Cited

U.S. PATENT DOCUMENTS

| | | |
|---|---|---|
| 3,492,258 | 1/1970 | Kremer . |
| 3,833,406 | 9/1974 | White . |
| 4,036,360 | 7/1977 | Deffeyes . |
| 4,407,897 | 10/1983 | Farrell et al. . |
| 4,730,726 | 3/1988 | Holzwarth . |
| 4,792,484 | 12/1988 | Moritani . |
| 4,894,277 | 1/1990 | Akasaki . |
| 4,935,346 | 6/1990 | Phillips et al. . |
| 4,970,172 | 11/1990 | Kundu ................................ 422/60 |
| 5,002,792 | 3/1991 | Vegoe . |
| 5,049,487 | 9/1991 | Phillips et al. . |
| 5,078,909 | 1/1992 | Shigeta et al. . |
| 5,108,706 | 4/1992 | Saggiorato . |
| 5,147,698 | 9/1992 | Cole . |
| 5,238,652 | 8/1993 | Sun et al. ............................ 422/61 |
| 5,304,419 | 4/1994 | Shores . |
| 5,304,468 | 4/1994 | Phillips et al. . |
| 5,460,777 | 10/1995 | Kitajima et al. ..................... 422/58 |
| 5,500,470 | 3/1996 | Mirle et al. . |
| 5,516,390 | 5/1996 | Tomita et al. . |

FOREIGN PATENT DOCUMENTS

WO 96/29603  9/1996  WIPO .

*Primary Examiner*—Lyle A. Alexander
*Attorney, Agent, or Firm*—Ratner & Prestia

[57] ABSTRACT

Medical diagnostic test strips having a desiccant deposit applied directly to the test strip. Moisture barrier sheets cover the test strip. Alternatively, the moisture barrier sheets have a desiccant deposit attached to them. Also alternatively, a pouch with a desiccant deposit attached to its inner surface contains the test strip.

15 Claims, 4 Drawing Sheets

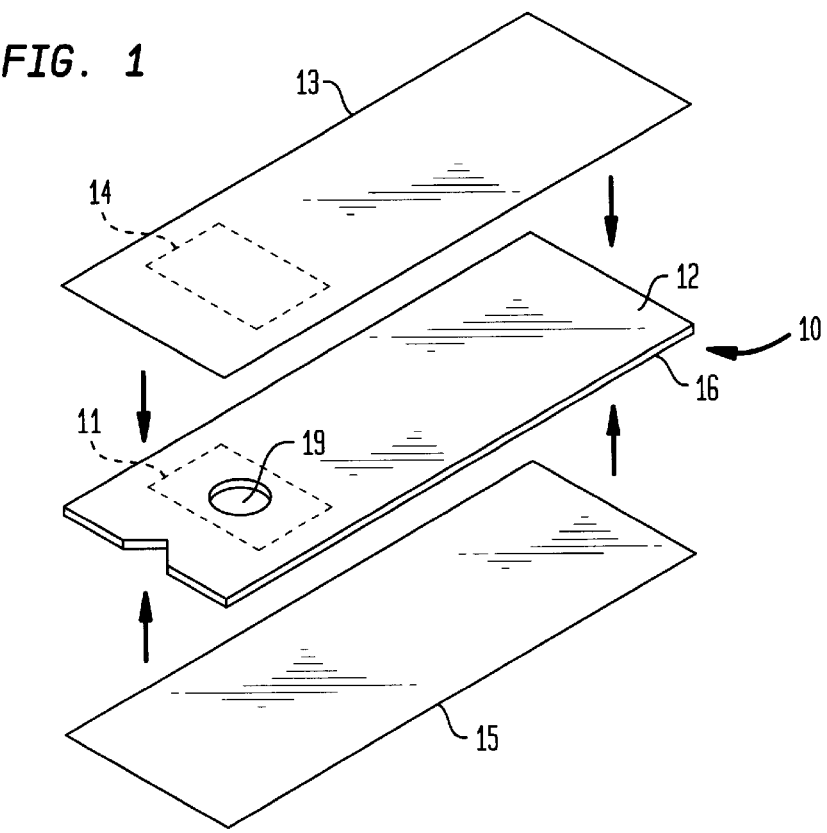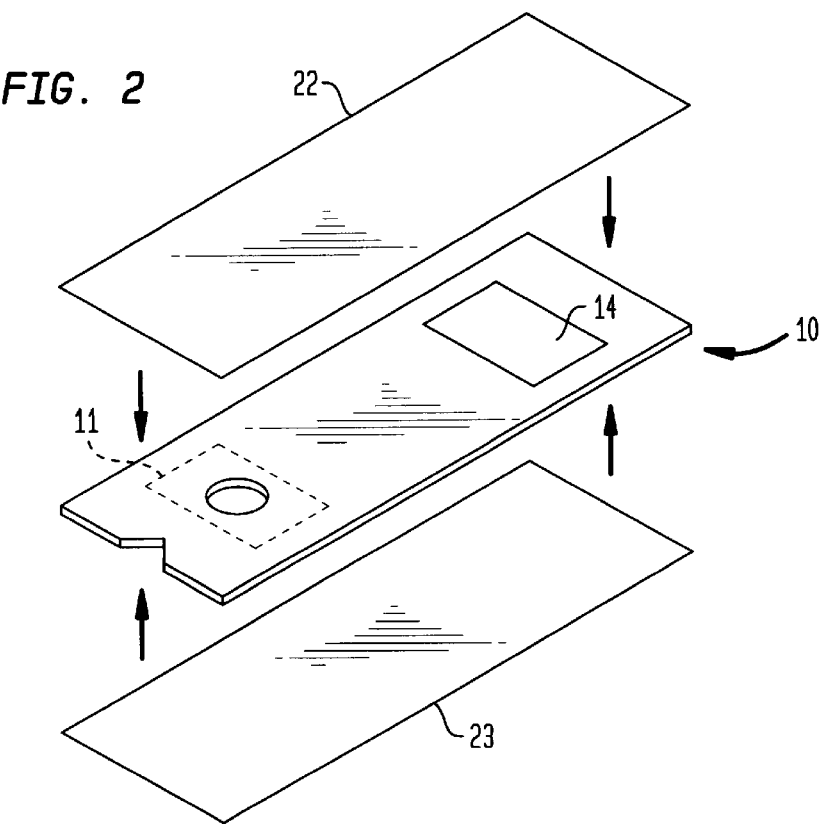

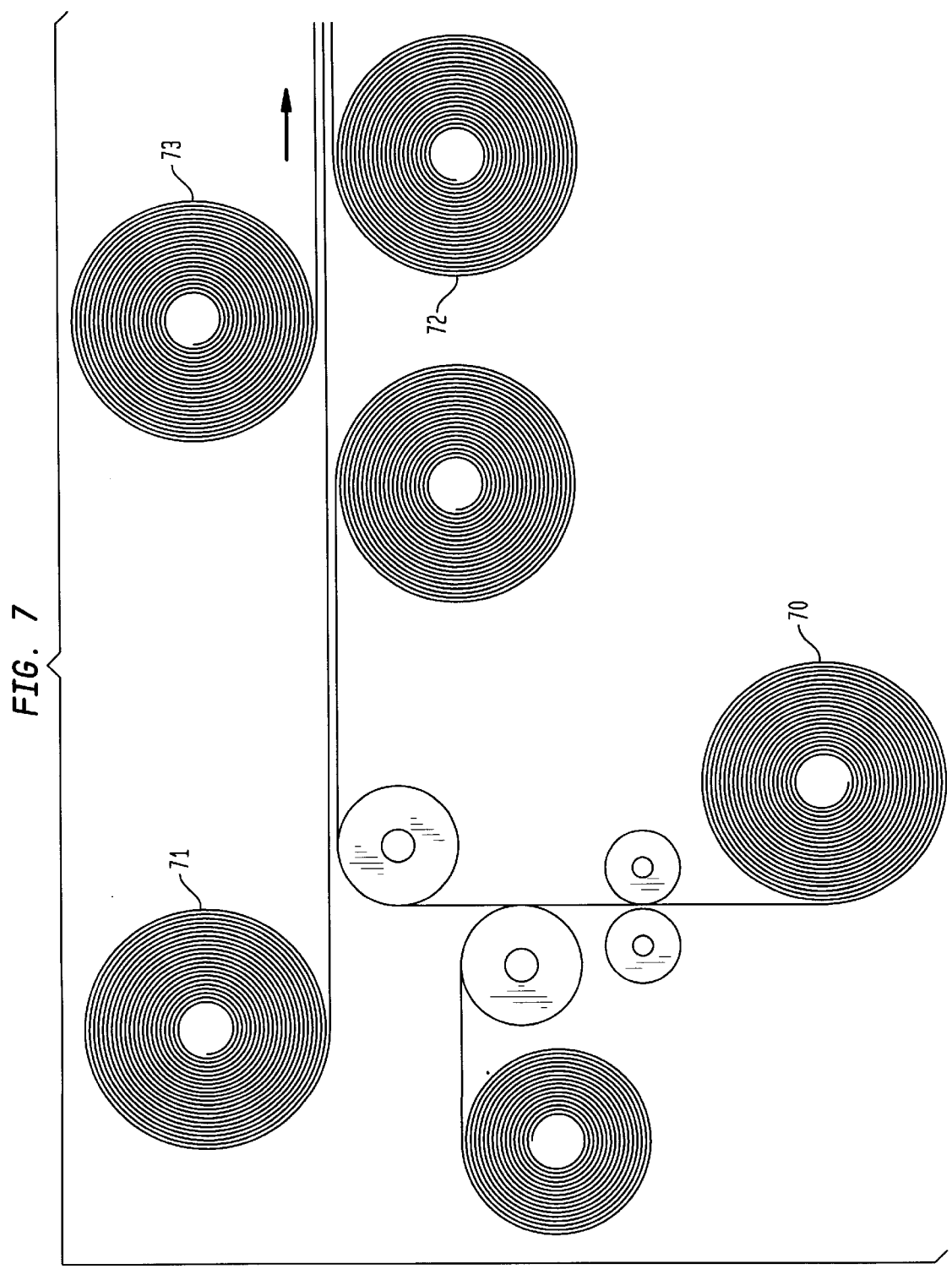

MEDICAL DIAGNOSTIC TEST STRIP WITH DESICCANT

This application claims the benefit of U.S. Provisional Application No. 60/010,548, filed Jan. 25, 1996, and U.S. application Ser. No. 60/016,996, filed Apr. 30, 1996, both entitled MEDICAL DIAGNOSTIC TEST STRIP WITH DESICCANT.

FIELD OF THE INVENTION

This invention relates to medical diagnostic test strips and, more particularly, to a medical diagnostic test strip package having a desiccant disposed in close proximity to the reagents on the test strip such that single strip manufacturing, packaging, shipping, and use is feasible.

BACKGROUND OF THE INVENTION

Medical diagnostic test strips are used in a variety of applications. Such strips are exposed to samples of blood, feces, or urine, for example, where specific reagents on the test strip are designed to detect various components in the sample. Medical diagnostic test strips are specifically used to detect the level of glucose in a patient's blood. Such test strips must be exposed to an atmosphere that is substantially moisture-free until moments before use in testing a sample. The strips are often highly water absorbent, and absorption of moisture may alter test results.

Accordingly, the known industry practice for keeping the test strips dry is to contain a plurality of such test strips in a container or vial. The cap for the container has a desiccant contained in it to absorb water from the air inside the container. In this manner, the strips within the container are kept dry. When ultimately used, a doctor or other testing personnel, including a patient himself, removes the cap from the container, extracts one of the test strips, and immediately places it in the sample to be tested (or places a small quantity of the sample to be tested on the test strip) Exposure of the strips to the ambient atmosphere before use is thus minimized to reduce water vapor absorption by the test strip.

A disadvantage of this technique is that all of the strips within the vial must be used within a relatively short time after the vial is first opened or they cannot be reliably used. The time period is usually on the order of a few months. Because of the exposure to the ambient atmosphere upon opening, there is a risk that the test strips will absorb enough moisture to render them ineffective in this amount of time despite the presence of the desiccant in the cap. In addition, there are manufacturing, packaging, and use complications resulting from the inclusion of multiple test strips in a single vial according to prior practice. It is therefore desirable to provide individual test strips with the ability to resist water absorption. This would provide efficiencies in manufacturing, packaging, and using the strips.

SUMMARY OF THE INVENTION

The present invention involves packaging individual test strips such that the test strips remain in a moisture-free environment. This is accomplished by applying a desiccant deposit directly to the test strip and covering the test strip with moisture barrier sheets, by using moisture barrier sheets having a desiccant deposit attached to them, or by forming a pouch with a desiccant deposit attached to an inner surface of the pouch and placing the test strip within the pouch.

BRIEF DESCRIPTION OF THE FIGURES

FIG. 1 is a perspective view of a first exemplary embodiment of the present invention;

FIG. 2 is a perspective view of a second exemplary embodiment of the present invention;

FIG. 7 is a schematic view of a system for making a medical diagnostic test strip package according to an exemplary embodiment of the present invention.

DETAILED DESCRIPTION OF THE INVENTION

According to the present invention, individual medical diagnostic test strips are packaged in a moisture-free environment by disposing a desiccant in close proximity to the reagents used on the test strip. FIG. 1 shows a first exemplary embodiment of the present invention. In FIG. 1, test strip 10 is shown having reagent pad 11 attached to it. Reagent pad 11 contains the particular compounds necessary to perform the desired detection test for a sample in a particular application. In some cases, depending on the particular reagents used, reagent pad 11 changes color upon exposure to the test sample. This color change can be observed and possibly measured to yield information regarding the presence or amount of the component being measured. In other cases, other measurable or observable characteristics of reagent pad 11, such as reflectance, may change upon exposure to the test sample and thereby yield the desired information regarding the sample.

Exemplary test strips and reagent pads used to measure the amount of glucose in the blood, and the manufacture and use of such test strips and reagent pads, are described in U.S. Pat. Nos. 4,935,346; 5,049,487; and 5,304,468, all of which are hereby incorporated by specific reference for their teachings on the manufacture and use of test strips and reagent pads.

Figure 6:
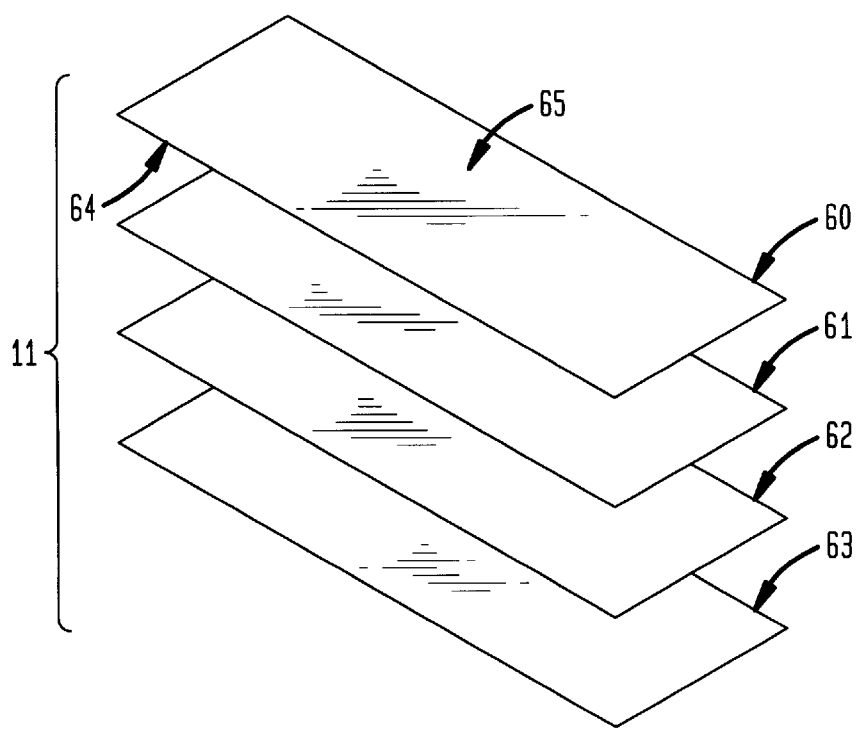
FIG. 6 is a perspective view of a reagent pad used with a test strip in an exemplary embodiment of the present invention.

Alternatively, reagent pad 11 may have the structure shown in FIG. 6. In FIG. 6, upper liner 60 is typically formed of polyethylene terephthalate (or PET) and has a conventional cold or hot melt adhesive on its bottom surface 64. A reagent paper layer 61, having the required reagents for a particular application on it, is adhered to bottom surface 64 of upper liner 60. A double-sided tape layer 62 is used to adhere reagent paper layer 61 to lower liner 63, which is typically formed of PET. After assembly of the composite layers shown in FIG. 6, reagent pad 11 is adhered to test strip 10 by conventional cold or hot melt adhesives placed around the edges of upper surface 65 of upper liner 60. Test strip 10 has a hole 19 formed in it to access reagent pad 11.

Figure 4:
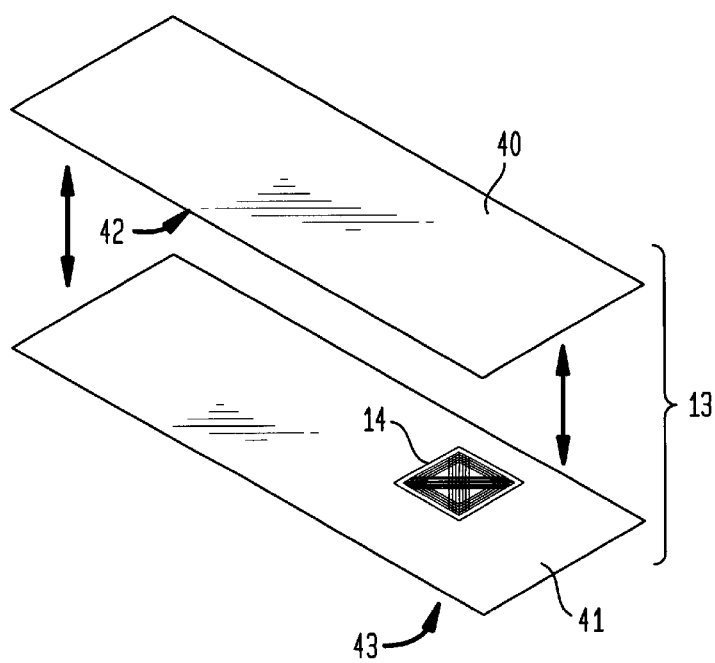
FIGS. 4 and 5 are perspective views of moisture barrier sheets used in an exemplary embodiment of the present invention.

The top surface 12 of test strip 10 has a top sheet 13 adhered to it. Top sheet 13 is adhered to test strip 10 by any conventional cold adhesive or hot melt adhesive known in the art. FIG. 4 shows an exemplary construction for top sheet 13. In FIG. 4, top sheet 13 is shown to have a two-part composite structure. Upper composite layer 40 is formed of foil to provide a moisture barrier. Upper composite layer 40 has a conventional cold or hot melt adhesive on its bottom surface 42. The adhesive is used to attach upper composite layer 40 to a lower composite layer 41.

Lower composite layer 41 is a microperforated layer typically made of parchment paper or Mylar® film. Lower composite layer 41 also has a conventional cold or hot melt adhesive on its bottom surface 43 to attach lower composite layer 41 (and hence top sheet 13) to test strip 10. Lower composite layer 41 has a desiccant deposit 14 adhered to it. Desiccant deposit 14 comprises a silica gel (or other particle remover such as a molecular seive or an oxygen absorber) dispersed in a medium suitable for suspending the silica gel and allowing adhesion of desiccant deposit 14 to lower composite layer 41. In the exemplary embodiment shown, the medium comprises vinyl acetate and a hot melt adhesive. As shown in FIG. 1, desiccant deposit 14 is located within top sheet 13 such that, upon application of top sheet 13 to test strip 10, desiccant deposit 14 is adjacent to reagent pad 11.

Figure 5:
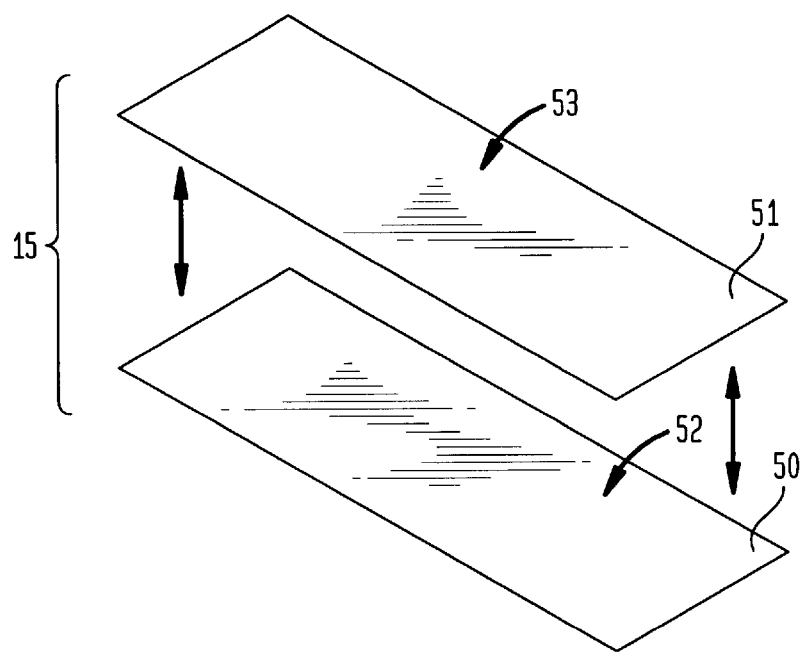

FIG. 1 shows a bottom sheet 15 adhered to the side of test strip 10 opposite upper surface 12. Bottom sheet 15 has an exemplary construction shown in FIG. 5. In FIG. 5, lower composite layer 50 is made of foil and forms a moisture barrier. Upper surface 52 of lower composite layer 50 has a conventional cold or hot melt adhesive on it to adhere lower composite layer 50 to upper composite layer 51. Upper composite layer 51 is a microperforated layer typically formed of parchment paper or Mylar® film, and has an upper surface 53 with a conventional cold or hot melt adhesive on it to adhere upper composite layer 51 (and hence bottom sheet 15) to test strip 10.

Top sheet 13 and bottom sheet 15 are moisture barriers that prevent any water from contacting, and being absorbed by, test strip 10. In the event that test strip 10 is exposed to any moisture, desiccant deposit 14 absorbs the moisture rather than reagent pad 11. Desiccant deposit 14 may also alternatively be applied to bottom sheet 15, or to both top sheet 13 and bottom sheet 15.

Test strip 10, with top sheet 13 and bottom sheet 15 adhered to it and with desiccant deposit 14 in top sheet 13, may be manufactured and shipped individually, along with other test strips. An exemplary manufacturing process is schematically illustrated in FIG. 7. As shown in FIG. 7, press rolls may be used to produce a test strip package according to the present invention. Roll 70 is a rolled length of the composite reagent pad 11 described in connection with FIG. 6 Roll 71 is a rolled length of polyvinylchloride (or PVC) strip stock of which test strip 10 may be formed. Roll 70 is unwound and cut into reagent pads 11 of appropriate size. Reagent pads 11 are then pressed onto PVC test strip material unwound from roll 71. Simultaneously, roll 73 of a length of upper sheet 13, and roll 72 of a length of bottom sheet 15 are unwound, and sheets 13 and 15 are pressed onto the top surface 12 and the bottom surface 16, respectively, of the length of test strip material with reagent pads 11.

To use test strip 10, the doctor or other testing personnel peels off top sheet 13 and bottom sheet 15, much like with a Band-Aid® bandage, and inserts test strip 10 into a sample for testing (or places the sample on test strip 10).

FIG. 2 illustrates a second embodiment of the present invention. In FIG. 2, test strip 10 has desiccant deposit 14 applied directly to it. Desiccant deposit 14 has the same composition as described in connection with the exemplary embodiment of FIG. 1. With the exemplary embodiment shown in FIG. 2, top sheet 22 and bottom sheet 23 are applied to the top and bottom surfaces 12 and 16, respectively, of test strip 10. Top sheet 22 and bottom sheet 23 are moisture barriers, and may have a composite construction as described in connection with bottom sheet 15 in the exemplary embodiment of FIG. 5.

In use, top sheet 22 and bottom sheet 23 are peeled away from test strip 10 by the doctor or other testing personnel. Test strip 10, with desiccant deposit 14 adhered thereto, is then inserted into the sample for testing (or the sample is placed on reagent pad 11 of test strip 10).

Alternatively, desiccant deposit 14 may comprise a hot melt adhesive with a desiccant dispersed in it. Any known hot melt adhesive and desiccant can be used for this purpose. The adhesive may serve an adhesive function, for example, to help secure top sheet 22 or bottom sheet 23 to test strip 10 Alternatively, the adhesive may be allowed to dry before application of top sheet 22 or bottom sheet 23 and serve only as a carrier for the desiccant and not as an adhesive.

Figure 3:
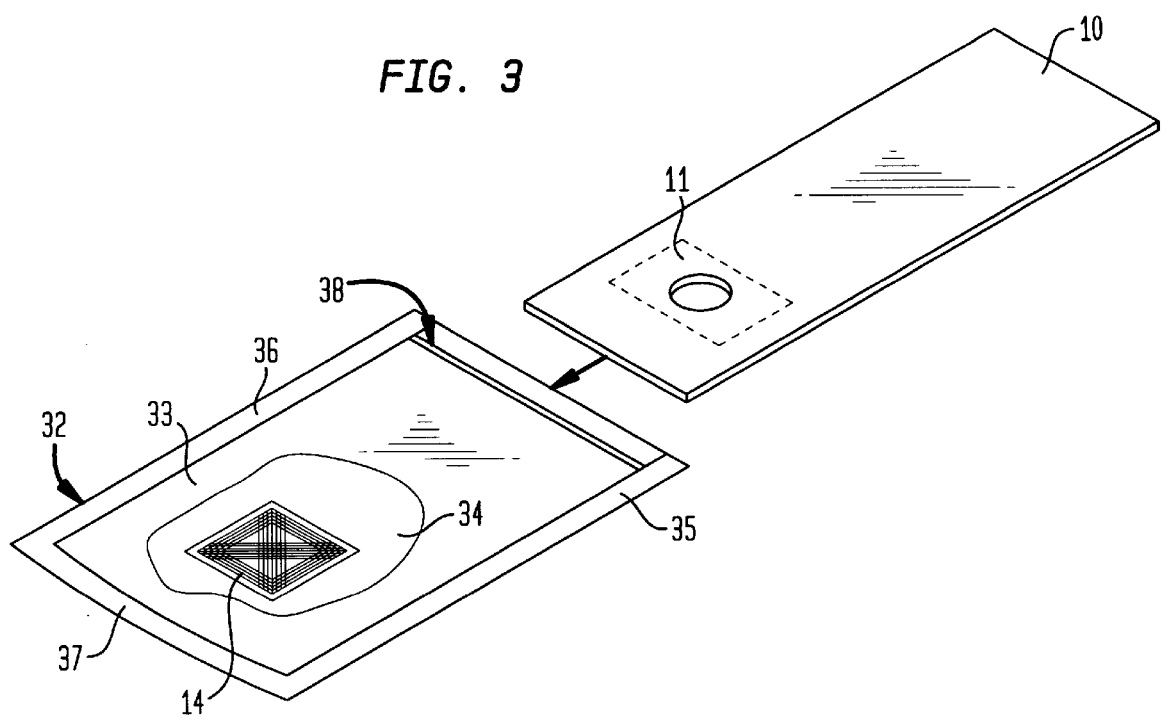
FIG. 3 is a partially cut-away perspective view of a third exemplary embodiment of the present invention.

FIG. 3 illustrates a third embodiment of the present invention. In FIG. 3, test strip 10 with reagent pad 11 is shown with a pouch 32 which is designed to contain test strip 10. Pouch 32 is formed of top sheet 33 and bottom sheet 34 which are adhered together along three of their edges to form seals 35, 36, and 37. The remaining edge of top sheet 33 and bottom sheet 34 on one side of the pouch is closed using a reclosable ziplock opening 38. Reclosable ziplock opening 38 allows access to the interior of pouch 32. Desiccant deposit 14 is formed on the inside of the pouch on top sheet 33, bottom sheet 34, or both. Desiccant deposit 14 may have the same composition as described above in connection with FIG. 1. Top sheet 33 and bottom sheet 34 are moisture barriers that may have the composite structure described for bottom sheet 15 in connection with FIG. 5. In use, the doctor or other testing personnel opens reclosable ziplock opening 38 and removes test strip 10. Test strip 10 is then immediately placed in a sample for testing (or the sample is placed on reagent pad 11 of test strip 10).

Alternatively, desiccant deposit 14 may comprise a hot melt adhesive with a desiccant dispersed in it. Any known hot melt adhesive and desiccant can be used for this purpose. The adhesive may serve an adhesive function, for example, to help secure top sheet 33 or bottom sheet 34 of pouch 32 to the test strip. The adhesive also may be allowed to dry before insertion of test strip 10 into pouch 32 and serve only as a carrier for the desiccant and not as an adhesive.

In the embodiments of the present invention discussed above, only one desiccant deposit is illustrated in each case. Additional desiccant deposits may be included in any of the embodiments as necessary for a particular application.

EXAMPLE 1

A desiccant deposit was formed by dispersing different amounts of silica gels in vinyl acetate by mixing the components in a conventional mixer until a homogeneous mixture was produced. The deposits were spread over a three square inch area using a draw-down bar by applying several thin layers over one another, allowing each layer to dry before applying the next layer. The weight of the deposits were measured at various times over a seven day period. Over the first four days, there was 40% relative humidity. The results are tabulated below. The increase in weight of the deposits reflects the amount of moisture absorbed. The data show good moisture absorption by the deposits.

ABSORPTION OF MOISTURE
BY A COATING CONTAINING SILICA GEL

| Sample | % of Silica Gel | Original Weight (grams) | 2 Days (grams) | 4 Days (grams) | 7 Days (grams) |
| --- | --- | --- | --- | --- | --- |
| #1 | 50% | .303 | .303 | .304 | .306 |
| #2 | 50% | .305 | .305 | .306 | .307 |

-continued

ABSORPTION OF MOISTURE
BY A COATING CONTAINING SILICA GEL

| Sample | % of Silica Gel | Original Weight (grams) | 2 Days (grams) | 4 Days (grams) | 7 Days (grams) |
|---|---|---|---|---|---|
| #3 | 50% | .318 | .318 | .320 | .349 |
| #4 | 35% | .313 | .313 | .314 | .314 |
| #5 | 35% | .317 | .317 | .318 | .319 |
| #6 | 35% | .319 | .320 | .321 | .323 |

1,2,3: 50% 7–10 micron Grace Syloid AL-1 silica gel in B-15 vinyl acetate homopolymer (available from Air Products), ethanol used as the solvent.
4,5,6: 35% 7–10 micron Grace Syloid AL-1 silica gel in B-15 vinyl acetate homopolymer (available from Air Products), ethanol used as the solvent.

EXAMPLE 2

A desiccant deposit was made by dispersing 41% by weight 50 mesh silica gel (non-indicating) in a conventional hot melt adhesive. Three samples were produced and deposited as drops on foil for moisture absorption testing. The results are tabulated below.

| Sample number: | 1 | 2 | 3 |
|---|---|---|---|
| Resin weight (g): | 4.45 | 4.14 | 4.17 |
| Total sample weight (g): | 5.01 | 4.78 | 4.71 |
| Moisture absorbed after 5 days (g): | 0.02 | 0.03 | 0.03 |
| Moisture absorbed after 10 days (g): | 0.05 | 0.05 | 0.04 |
| Moisture absorbed after 17 days (g): | 0.08 | 0.08 | 0.08 |
| Moisture absorbed after 21 days (g): | 0.09 | 0.09 | 0.09 |

EXAMPLE 3

A desiccant deposit was made by dispersing 40% by weight 50 mesh silica gel (non-indicating) in H. B. Fuller HM 1072 hot melt adhesive. Three samples were produced and deposited as drops on foil for moisture absorption testing. The results are tabulated below.

| Sample number: | 1 | 2 | 3 |
|---|---|---|---|
| Resin weight (g): | 5.39 | 4.05 | 4.14 |
| Total sample weight (g): | 6.09 | 4.74 | 4.73 |
| Moisture absorbed after 5 days (g): | 0.08 | 0.05 | 0.04 |
| Moisture absorbed after 10 days (g): | 0.12 | 0.09 | 0.08 |
| Moisture absorbed after 17 days (g): | 0.16 | 0.11 | 0.09 |
| Moisture absorbed after 21 days (g): | 0.19 | 0.14 | 0.10 |

EXAMPLE 4

Another desiccant deposit was made by dispersing 40% by weight 50 mesh silica gel (non-indicating) in H. B. Fuller HM 1072 hot melt adhesive. Three samples were produced and deposited as drops on foil for moisture absorption testing. The results are tabulated below.

| Sample number: | 1 | 2 | 3 |
|---|---|---|---|
| Resin weight (g): | 3.90 | 4.46 | 3.45 |
| Total sample weight (g): | 4.58 | 5.04 | 4.05 |
| Moisture absorbed after 5 days (g): | 0.08 | 0.06 | 0.05 |
| Moisture absorbed after 10 days (g): | 0.13 | 0.12 | 0.09 |
| Moisture absorbed after 17 days (g): | 0.16 | 0.14 | 0.12 |
| Moisture absorbed after 21 days (g): | 0.17 | 0.17 | 0.12 |

EXAMPLE 5

A desiccant deposit was made by dispersing 40% by weight 50 mesh silica gel in Eco hot melt adhesive. Three samples were produced and deposited as drops on foil for moisture absorption testing. The results are tabulated below.

| Sample number: | 1 | 2 | 3 |
|---|---|---|---|
| Resin weight (g): | 4.15 | 3.47 | 5.06 |
| Total sample weight (g): | 4.70 | 4.06 | 5.62 |
| Moisture absorbed after 5 days (g): | 0.00 | 0.05 | 0.07 |
| Moisture absorbed after 10 days (g): | 0.05 | 0.11 | 0.11 |
| Moisture absorbed after 17 days (g): | 0.13 | 0.13 | 0.16 |
| Moisture absorbed after 21 days (g): | 0.15 | 0.13 | 0.18 |

EXAMPLE 6

A desiccant deposit was made by dispersing 40% by weight indicating silica gel in store-bought hot melt adhesive. Three samples were produced and deposited as drops on foil for moisture absorption testing. The results are tabulated below.

| Sample number: | 1 | 2 | 3 |
|---|---|---|---|
| Resin weight (g): | 4.31 | 3.91 | 3.99 |
| Total sample weight (g): | 4.82 | 4.48 | 4.57 |
| Moisture absorbed after 5 days (g): | 0.16 | 0.15 | 0.17 |
| Moisture absorbed after 10 days (g): | 0.22 | 0.86 | 0.24 |
| Moisture absorbed after 17 days (g): | 0.28 | 0.90 | 0.28 |
| Moisture absorbed after 21 days (g): | 0.31 | 0.93 | 0.30 |

EXAMPLE 7

A desiccant deposit was made by dispersing 40% by weight 50 mesh non-indicating silica gel in store-bought hot melt adhesive. Three samples were produced and deposited as drops on foil for moisture absorption testing. The results are tabulated below.

| Sample number: | 1 | 2 | 3 |
|---|---|---|---|
| Resin weight (g): | 3.79 | 3.91 | 4.45 |
| Total sample weight (g): | 4.34 | 4.48 | 5.12 |
| Moisture absorbed after 5 days (g): | 0.12 | 0.15 | 0.13 |
| Moisture absorbed after 10 days (g): | 0.16 | 0.20 | 0.19 |
| Moisture absorbed after 17 days (g): | 0.23 | 0.25 | 0.24 |
| Moisture absorbed after 21 days (g): | 0.24 | 0.27 | 0.25 |

EXAMPLE 8

A desiccant deposit was made by dispersing 40% by weight indicating silica gel in a conventional hot melt adhesive. Three samples were produced and deposited as drops on foil for moisture absorption testing. The results are tabulated below.

| Sample number: | 1 | 2 | 3 |
|---|---|---|---|
| Resin weight (g): | 5.09 | 4.49 | 4.93 |
| Total sample weight (g): | 5.70 | 5.16 | 5.50 |
| Moisture absorbed after 5 days (g): | 0.04 | 0.05 | 0.04 |
| Moisture absorbed after 10 days (g): | 0.07 | 0.22 | 0.07 |
| Moisture absorbed after 17 days (g): | 0.10 | 0.23 | 0.10 |
| Moisture absorbed after 21 days (g): | 0.12 | 0.12 | 0.11 |

EXAMPLE 9

A desiccant deposit was made by dispersing 40% by weight indicating silica gel in FPC 725 hot melt adhesive.

Three samples were produced and deposited as drops on foil. Additional silica gel was sprinkled on top of the drops. Moisture absorption test results are tabulated below.

| Sample number: | 1 | 2 | 3 |
|---|---|---|---|
| Weight of foil (g): | 0.62 | 0.56 | 0.62 |
| Weight of foil, resin, and gel (g): | 5.75 | 6.85 | 7.20 |
| Weight with sprinkled gel (g): | 6.41 | 7.50 | 7.66 |
| Moisture absorbed after 3 days (g): | 0.35 | 0.38 | 0.10 |
| Moisture absorbed after 7 days (g): | 0.36 | 0.43 | 0.10 |

EXAMPLE 10

A desiccant deposit was made of FPC 725 hot melt adhesive. Three samples were produced and deposited as drops on foil. Silica gel was sprinkled on top of the drops. Moisture absorption test results are tabulated below.

| Sample number: | 1 | 2 | 3 |
|---|---|---|---|
| Weight of foil (g): | 0.54 | 0.62 | 0.45 |
| Weight of foil, resin, and gel (g): | 4.23 | 6.91 | 3.50 |
| Weight with sprinkled gel (g): | 6.41 | 7.50 | 7.66 |
| Moisture absorbed after 3 days (g): | 0.13 | 0.26 | 0.07 |
| Moisture absorbed after 7 days (g): | 0.13 | 0.26 | 0.07 |

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. In particular, the invention is intended to incorporate moisture and particle absorption from any flat medical diagnostic product.

What is claimed:

1. A medical diagnostic test strip package comprising:
   (a) a medical diagnostic test strip having a top surface, a reagent contained on a portion of said top surface, and a bottom surface; and
   (b) a first moisture barrier sheet adhered to said top surface of said medical diagnostic test strip, said first moisture barrier sheet having a desiccant deposit adhered to a portion thereof such that said portion of said first moisture barrier sheet with said desiccant deposit thereon is integrally disposed on said portion of said medical diagnostic test strip containing said reagent.

2. A medical diagnostic test strip package as claimed in claim 1 further comprising a second moisture barrier sheet adhered to said bottom surface of said medical diagnostic test strip.

3. A medical diagnostic test strip package as claimed in claim 1 wherein said desiccant is silica gel.

4. A medical diagnostic test strip package as claimed in claim 1 wherein said desiccant is molecular sieve.

5. A medical diagnostic test strip package as claimed in claim 1 wherein said desiccant is dispersed in a hot melt adhesive.

6. A medical diagnostic test strip package comprising:
   (a) a medical diagnostic test strip having
      (i) a top surface,
      (ii) a reagent contained in a first portion of said top surface,
      (iii) a desiccant deposit adhered to a second portion of said top surface, said second portion adjacent to said first portion, and
      (iv) a bottom surface; and
   (b) a first moisture barrier sheet adhered to said top surface of said medical diagnostic test strip.

7. A medical diagnostic test strip package as claimed in claim 6 further comprising a second moisture barrier sheet adhered to said bottom surface of said medical diagnostic test strip.

8. A medical diagnostic test strip package as claimed in claim 6 wherein said desiccant is silica gel.

9. A medical diagnostic test strip package as claimed in claim 6 wherein said desiccant is molecular sieve.

10. A medical diagnostic test strip package as claimed in claim 6 wherein said desiccant is dispersed in a hot melt adhesive.

11. A medical diagnostic test strip package comprising:
    (a) a medical diagnostic test strip having a top surface and a reagent contained in a first portion of said top surface, and
    (b) a pouch containing said medical diagnostic test strip, said pouch having an inner surface and a desiccant deposit adhered to a section of said inner surface, wherein said inner surface of said pouch is disposed proximate said top surface of said medical diagnostic test strip such that said desiccant deposit is adjacent to said reagent of said test strip.

12. A medical diagnostic test strip package as claimed in claims 11 wherein said desiccant is silica gel.

13. A medical diagnostic test strip package as claimed in claim 11 wherein said desiccant is molecular sieve.

14. A medical diagnostic test strip package as claimed in claim 11 wherein said desiccant is dispersed in a hot melt adhesive.

15. A method of preventing water absorption by a medical diagnostic test strip having a top surface, a bottom surface, and a portion of said top surface containing a reagent, said method comprising the steps of:
    (a) covering said top surface with a first moisture barrier sheet;
    (b) covering said bottom surface with a second moisture barrier sheet; and
    (c) integrally disposing a desiccant deposit in proximity to said portion of said top surface of said medical diagnostic test strip containing the reagent.

* * * * *